US00PP09677P

United States Patent [19]

Osiecki

[11] Patent Number: Plant 9,677

[45] Date of Patent: Oct. 29, 1996

[54] SPATHIPHYLLUM PLANT 'S8'

[75] Inventor: Marian W. Osiecki, Marianna, Fla.

[73] Assignee: Oglesby Plant Laboratories, Inc., Altha, Fla.

[21] Appl. No.: 525,433

[22] Filed: Sep. 6, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz, PC

[57] ABSTRACT

A new and distinct cultivar of Spathiphyllum is provided. This new cultivar is a medium size, full plant, suitable for production in 15 cm and 20 cm pots from a single tissue cultured microcutting with vigorous growth, early and abundant branching, early flowering, dark green, glossy, slightly recurvate leaves and numerous attractive inflorescences year-round.

2 Drawing Sheets

SUMMARY OF THE INVENTION

This invention relates to a new and distinct Spathiphyllum cultivar characterized by the following combination of repeatedly observed traits:

1. Medium size, full plant
2. Vigorous growth
3. Early and abundant branching
4. Early, abundant and year-round natural flowering
5. Deep dark green, glossy foliage year-round
6. Slightly recurvate leaves
7. Medium size spathes of a good quality from the onset of flowering, held relatively high above foliage and primarily selected for those characteristics being so selected from the progeny of the cross stated below grown near Altha, Fla. in a cultivated area.

ORIGIN AND ASEXUAL REPRODUCTION

Asexual reproduction of this cultivar by tissue culture was directed by me, such reproduction establishing that the plant does in fact maintain the characteristics described, in successive generations. The plant was initially selected where grown in a planned breeding program in or near Altha, Fla. and has since been reproduced by tissue culture in the vicinity of Altha, Fla. with the characteristics stated.

The female parent was selected clone of Spathiphyllum 'Petite' and the male parent was a selected clone of Spathiphyllum 'Supreme'. The cross was made in 1991, the seedling was selected in 1992.

This new cultivar has been identified as Spathiphyllum 'S8'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S8' was approximately 17 months from planting a tissue cultured microcutting and grown in a 20 cm pot.

In the photographs:

FIG. 1 depicts the whole plant;

FIG. 2 illustrates the mature inflorescence;

FIG. 3 illustrates the top of a mature leaf; and

FIG. 4 illustrates the bottom of a mature leaf.

DETAILED DESCRIPTION OF THE NEW CULTIVAR

The following observations and measurements describe plants grown near Altha, Fla. under greenhouse conditions. These observations and measurements were recorded in August 1994 from mature plants (about 10.5 months from planting tissue cultured microcuttings) grown in 15 cm pots. Fully developed organs were used for measurements. Color values were determined on Aug. 25, 1994 under natural, indirect light of 700–800 foot candles. Color references are made to the R.H.S. Color Chart, except where general color terms of ordinary significance are used.

'S8' has not been observed under all possible environmental conditions. The phenotype may vary with variations in environment and horticultural practices, such as temperature, light intensity, day length, fertilization etc., without any change in genotype.

Parentage:

*Female parent.*—Spathiphyllum 'Petit'.

*Male parent.*—Spathiphyllum 'Supreme'.

Propagation: Plant tissue culture started near Altha, Fla.

Plant Descriptions:

*Growth habit.*—Medium size, full, very well branched, shoots erect with slightly recurvate leaves.

*Height.*—Foliage 34–47 cm, with spathes 57–70 cm.

*Diameter.*—49–61 cm.

Petiole.

*Size.*—20.0–29.0 cm long.

*Geniculum.*3.5–4.5 cm long.

Leaf blade:

*Shape.*—Elliptic to lanceolate, sometimes slightly asymmetric; tip acuminate, base cuneate with obtuse tendencies, narrowly decurrent on peduncle. Many apices slightly curved. Leaves produced before the onset of flowering are more linear and have more acute bases.

*Size.*—21.3–23.5 cm long by 7.2–9.0 cm wide; length: width ratio 2.5–3.1:1.

*Texture.*—Smooth, glossy; young leaves highly polished.

*Veins.*—Well defined and sunken.

*Color.*—Mature leaf: Adaxial surface: a littler darker than 147A (yellow-green). Abaxial surface: 147B (yellow-green). Newly unfolded leaf: Adaxial surface: lighter than 147A (yellow-green), but darker than 137A (green). Abaxial surface: approx. 147B (yellow-green).

Inflorescence:

*Arrangement.*—Spathes carried relatively high above foliage (distance between highest point of foliage and base of highest spathe 13–22 cm) on s ·ong straight peduncles. Spadix large in relation to spathe and situated relatively high on the spathe.

In a newly opened inflorescence, spadix and the edge of spathe are approximately in the same plane with peduncle or they slightly lean forward. As the inflorescence matures the spadix maintains an upright position and the spathe often leans backward from the juncture with stipe. At the time of pollen release spathe edges often form an angle of approximately 45° with the stipe.

Peduncle:

*Size.*52.5–63.0 cm long (including stipe).

*Stipe.*1.6–2.0 cm long (back side).

Spathe:

*Shape.*—Cupped; elliptic; tip—acuminate, slightly curled; base—cuneate with obtuse tendencies, sometimes slightly asymmetric, narrowly decurrent on peduncle.

*Size.*10.0–11.9 cm long by 5.3–6.0 cm wide; length: width ratio 1.7–2.2:1.

*Color.*—155A (white); adaxial side — upper ⅓ to ½ of the midrib very slightly green; abaxial side — a profoundly green zone extends from peduncle along midrib; it is 3–4 mm wide at the juncture with stipe, tapers toward tip becoming very light green in the upper part of the spathe and then widens and becomes more pronounced in the tip. The borders of the green zone are not clearly defined and its color is not uniform. It contains different shades of and between yellow–green (146A, B, 144A, B) and green (137B-D, 138A). A few lateral veins on the abaxial side are sometimes slightly green.

Spadix:

*Size.*—4.1–5.1 cm long; 1.2 cm–1.4 cm in diameter.

*Color.*158B (yellow-white).

Botanical Flower:

*Perianth.*—Inconspicuous (almost invisible between thick pistils), segments united.

*Pistil.*—Very thick, acute with some spherical tendencies, extrudes 2–3 mm beyond perianth, stigma large, well visible immediately after spathe opening.

*Stamens.*—Not visible before pollen release.

Flowering: Flowers naturally in 15 cm pots, about 8–10 months from tissue cultured microcuttings. Continuous year-round flowering. One to three white spathes constantly present above foliage.

Spathe longevity: Spathes remain white for 4.0–4.5 weeks following emergence of bud above foliage and then gradually change to a green color.

Roots: Thick, fleshy, white main roots, abundant fine lateral roots.

Disease and insect resistance: No unusual susceptibility to diseases or insects noted to date.

Comparison with the known cultivars: The new cultivar can be compared to the known cultivars 'Petite' and 'Viscount'. Observations for comparisons were made on plants grown under similar conditions in greenhouse near Altha, Fla.

'S8' is distinguished from both cultivars 'Petite' and 'Viscount' by its more vigorous growth, earlier and more abundant branching, fuller growth habit, more recurvate leaves, earlier, more abundant, year-round natural flowering. Within 10.5 months from tissue culture all plants of 'S8' had 1–3 open spathes, while neither 'Petite' nor 'Viscount' had started flowering. S8' is further distinguished from 'Petite' by its wider growth habit, darker, more glossy, longer and wider leaf blades.

'S8' is further distinguished from 'Viscount' by its shorter and narrower leaf blades.

I claim:

1. A new and distinct cultivar of Spathiphyllum plant named 'S8' as illustrated and described.

* * * * *

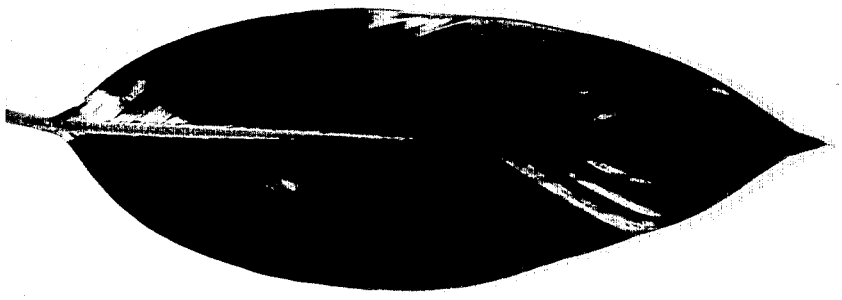
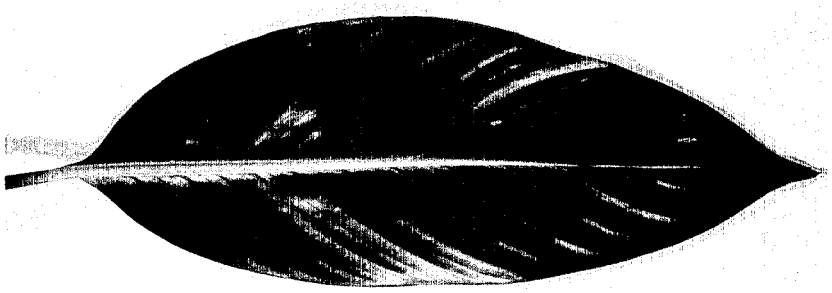

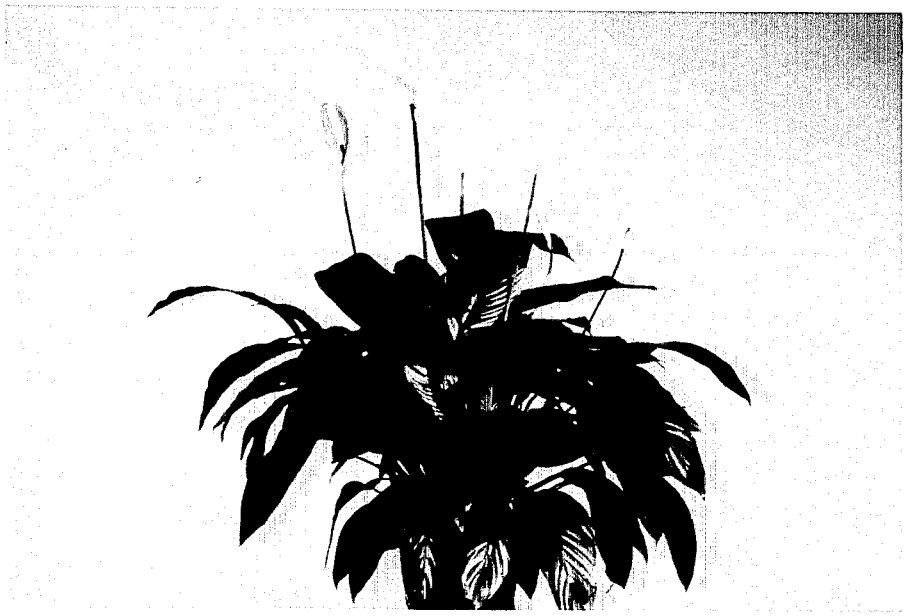
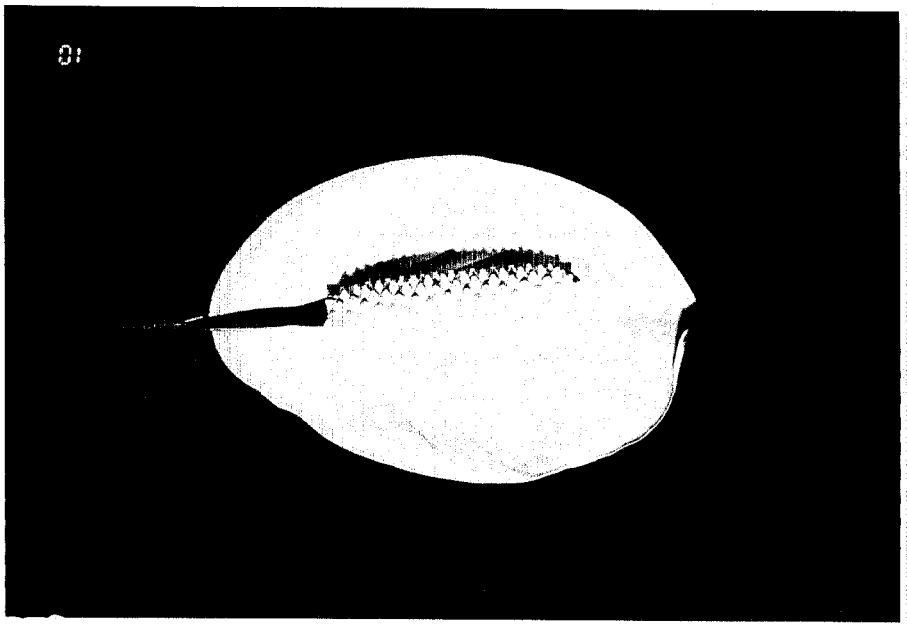
01